United States Patent
Opperman

(10) Patent No.: US 12,376,939 B2
(45) Date of Patent: Aug. 5, 2025

(54) METHOD OF MARKING A SPECIMEN

(71) Applicant: MarginView, LLC, Denver, CO (US)

(72) Inventor: David Opperman, Littleton, CO (US)

(73) Assignee: MarginView, LLC, Denver, CO (US)

( * ) Notice: Subject to any disclaimer, the term of this patent is extended or adjusted under 35 U.S.C. 154(b) by 459 days.

(21) Appl. No.: 18/045,162

(22) Filed: Oct. 9, 2022

(65) Prior Publication Data

US 2023/0310113 A1  Oct. 5, 2023

Related U.S. Application Data

(63) Continuation-in-part of application No. 17/805,716, filed on Jun. 7, 2022, and a continuation-in-part of application No. 16/711,653, filed on Dec. 12, 2019, now Pat. No. 11,464,599, which is a continuation-in-part of application No. 16/162,017, filed on Oct. 16, 2018, now abandoned, which is a continuation-in-part of application No. 15/139,012, filed on Apr. 26, 2016, now Pat. No. 10,111,727.

(60) Provisional application No. 63/213,168, filed on Jun. 21, 2021, provisional application No. 62/162,035, filed on May 15, 2015.

(51) Int. Cl.
A61B 90/00 (2016.01)

(52) U.S. Cl.
CPC ...... *A61B 90/39* (2016.02); *A61B 2090/3937* (2016.02); *A61B 2090/3987* (2016.02); *A61B 2090/3991* (2016.02)

(58) Field of Classification Search
CPC . A61B 90/39; A61B 90/92; A61B 2090/3991; A61B 2090/3987
See application file for complete search history.

(56) References Cited

U.S. PATENT DOCUMENTS

| | | |
|---|---|---|
| 4,041,931 A | 8/1977 | Elliot |
| 4,519,392 A | 5/1985 | Lingua |
| 5,474,569 A | 12/1995 | Zinreich |
| 5,702,128 A | 12/1997 | Maxim |
| D394,109 S | 5/1998 | Miller et al. |
| 5,902,310 A | 5/1999 | Foerster |
| D485,359 S | 1/2004 | McMichael et al. |
| 6,826,257 B2 | 11/2004 | Sayre |
| D625,005 S | 10/2010 | Zimmer et al. |
| D641,471 S | 6/2011 | Zimmer et al. |
| D643,118 S | 8/2011 | Zimmer et al. |
| D647,206 S | 10/2011 | Massad |

(Continued)

OTHER PUBLICATIONS

Office Action issued in related Israeli Patent Application No. 294155. Dec. 2024. 5 pages.

(Continued)

*Primary Examiner* — Phong Son H Dang
(74) *Attorney, Agent, or Firm* — FisherBroyles, LLP; Craig W. Mueller

(57) ABSTRACT

According to one embodiment, an apparatus is disclosed. The apparatus includes an endoscopic clip placement tool and one or more marking clips attached to a specimen mass by the clip placement tool to mark a margin and orientation of the specimen mass. A specimen marking clip is also provided that is adapted to selectively attach to tissue inside of a patient and corresponding tissue that has been excised from the patient for analysis. Sutures may be associated with the clips to help ensure correct in vivo and ex vivo sample orientation. In vivo clips may remain in the patient's body if necessary.

17 Claims, 15 Drawing Sheets

(56) References Cited

U.S. PATENT DOCUMENTS

| | | |
|---|---|---|
| D656,617 S | 3/2012 | Massad |
| D669,176 S | 10/2012 | Frey |
| 8,301,227 B2 | 10/2012 | Phillips |
| 8,579,922 B2 | 11/2013 | Glick |
| 8,594,768 B2 | 11/2013 | Phillips |
| 9,773,168 B2 | 9/2017 | Chatow |
| 10,111,727 B2 | 10/2018 | Opperman |
| 2004/0019360 A1 | 1/2004 | Farnsworth |
| 2004/0052333 A1 | 3/2004 | Sayre |
| 2005/0234336 A1 | 10/2005 | Beckman |
| 2006/0229529 A1 | 10/2006 | Wright |
| 2007/0088362 A1 | 4/2007 | Bonutti |
| 2007/0123915 A1 | 5/2007 | Kammerer |
| 2007/0232884 A1 | 10/2007 | Maschke |
| 2007/0270681 A1 | 11/2007 | Phillips |
| 2007/0276417 A1 | 11/2007 | Mendes |
| 2008/0103528 A1 | 5/2008 | Zirps |
| 2009/0099588 A1 | 4/2009 | Makower |
| 2010/0187284 A1 | 7/2010 | Crainich |
| 2010/0222802 A1 | 9/2010 | Gillespie |
| 2010/0305700 A1 | 12/2010 | Ben-Arye et al. |
| 2011/0082478 A1 | 4/2011 | Glick |
| 2011/0184441 A1 | 7/2011 | St-Germain |
| 2011/0301456 A1 | 12/2011 | Leclaire |
| 2014/0135773 A1 | 5/2014 | Stein |
| 2014/0276968 A1 | 9/2014 | Miksza |
| 2015/0157436 A1 | 6/2015 | Bailly |
| 2015/0374432 A1 | 12/2015 | Godara |

OTHER PUBLICATIONS

Non-Final Office Action from related U.S. Appl. No. 15/139,012, dated Jan. 8, 2018.
Non-Final Office Action from parent U.S. Appl. No. 16/162,017, filed Feb. 2, 2021. 12 pages.

es, patent
METHOD OF MARKING A SPECIMEN

This application is a continuation-in-part of U.S. patent application Ser. No. 16/711,653, filed Dec. 12, 2019, which is a continuation-in-part of abandoned U.S. patent application Ser. No. 16/162,017, filed Oct. 16, 2018, which is a continuation-in-part of U.S. patent application Ser. No. 15/139,012, filed Apr. 26, 2016, now U.S. Pat. No. 10,111,727, issued Oct. 30, 2018, which claims the benefit of U.S. Provisional Patent Application Ser. No. 62/162,035, filed May 15, 2015, the entire disclosures of which are incorporated by reference herein.

This application is also a continuation-in-part of U.S. patent application Ser. No. 17/805,716, filed Jun. 7, 2022, which claims the benefit of U.S. Provisional Patent Application Ser. No. 63/213,168, filed Jun. 21, 2021, the entire disclosures of which are incorporated by reference herein.

FIELD OF THE INVENTION

Embodiments of the present invention relates to medical devices, more particularly, surgical specimen margin orientation marking. Embodiments of the present invention are also generally related to medical devices, more particularly, surgical specimen margin marking and orientation devices and methods.

BACKGROUND

Surgical specimen margin orientation marking for endoscopic, robotic, laparoscopic, or other surgery types where body tissue is removed, is critical for pathological diagnosis, tumor excision, and other margin marking. One example of surgical specimen margin orientation marking may be featured in an endoscopic excision of a tumor. In such an example, the tumor is removed and forwarded to a pathologist for evaluation by frozen or permanent section. The pathologist subsequently performs an analysis to identify malignancy at one or more margins. A surgeon may then direct additional tissue to be excised, the orientation of which is critical for proper and accurate excision.

The current technique for surgical specimen margin orientation marking involves ink marking after a specimen has been removed from a body. FIG. 1 illustrates one embodiment of a conventional marking technique in which a specimen mass is marked with a dotted line to differentiate from surrounding tissues identifies an excised specimen mass. In such a technique an ink mark may be placed at "12:00 o'clock" position on the specimen mass.

However, this approach is inaccurate and subject to error if the orientation of the specimen is changed (e.g., dropped, manipulated, etc.). For example, it may be difficult to find the ink marks and compare to those on the removed specimen mass. Further, the surgeon, staff, or pathologist examining the specimen mass may mistakenly manipulate the removed specimen mass, or there may be miscommunication between surgeons and pathologists related to orientation. An alternative approach that may be implemented includes placement of a reference suture in the specimen at the 12:00 O'clock position. However, this approach is equally subject to error.

Accordingly, an improved surgical specimen margin orientation marking mechanism is desired. The systems and methods described herein allow for mirror image marking of multiple types of surgical specimens covering a multitude of surgeries and disciplines.

SUMMARY OF INVENTION

It is one aspect of some embodiments of the present invention to provide a marking clip configured to selectively engage tissue. The marking clip of one embodiment includes first and second legs extending from a common interconnection point. Opposite ends of the legs are spaced but can be selectively deformed toward each other when an external force is applied to the outside surfaces of the legs. In operation, tissue is placed between the legs and the clip is deformed, thereby pinching the tissue. In one embodiment, portions of the legs include teeth or a roughened/knurled surface that enhances grip. The legs and/or the common interconnection point may be more malleable to facilitate clip deformation.

A biopsied area of interest, e.g., a possibly cancerous mass, is removed from a patient's body along with a predefined amount of surrounding tissue. "Margin," as used herein, is the peripheral edge of the removed sample tissue, defined by the incision created to remove the tissue sample. Those of ordinary skill in the art will appreciate that accurate analysis, which is needed to ensure all abnormal tissue has been removed from the patient's body, is important and relies on maintaining tissue sample orientation. That is, understanding the orientation of the tissue sample relative to the excision location helps the surgeon and pathologist identify additional areas of concern on the tissue sample so that the surgeon can remove corresponding tissue from the patient.

Accordingly, it is another aspect of some embodiments to provide a clip that maintains the in vivo and ex vivo orientation of an excised tissue sample. More specifically, each clip of some embodiments of the present invention is of a unique color assigned to a predefined tissue sample attachment location on the margin. To further ensure proper post-excision tissue sample orientation, embodiments of the present invention interconnect like color clips to corresponding margin locations within the patient's body. One of ordinary skill in the art will appreciate that other means can be used to match ex vivo and in vivo clips.

Those of ordinary skill in the art will appreciate that other identification techniques may be used to define clip location on the tissue sample and in vivo. One embodiment, for example, employs colored sutures interconnected to otherwise indistinct clips. Other embodiments contemplate colored clips having sutures of matching colors extending therefrom. Alternatively, sutures positioned on one side of a margin (e.g., tissue sample side) may have one color/indicia and sutures positioned on the opposite side of the margin (e.g., in vivo side) may have a second color/indicia, thereby allowing quick identification of which suture to attach relative to the margin. Sutures may be striped with clip color to indicate their intended attachment location—in vivo or tissue sample side.

The clips may be made of material that suits the tissue to which they are to be attached—muscle, ligament, skin, fatty tissue, etc. The clips can be of any size and shape and made of any suitable material. For example, the clip's material of manufacture may be stiff, compliant, malleable, etc., to suit the surgeon's desires or to accommodate tissue character. In one embodiment, the clips are made of titanium per ASTM F67 Grade 1. The clips may possess a surface texture or other types of tactile or enhanced visual identification means. Further, the clips may be micro-engraved or X-ray marked with identifying information. The sutures also may employ microchip technology, nanotech technology, RFID technology, specialized coatings, frequency emitting devices that allow current or future-developed 3-dimensional, computer, or virtual reality medical imaging modalities to locate and identify sutures in the body. These marking methods may be provided in combination or in various sub-combinations.

The sutures of some embodiments of the present invention are stiff, compliant, malleable, etc., to suit the surgeon's desires. The sutures of one embodiment are made of PTFE coated braided polyester, meeting all requirements established by the United States Pharmacopedia (U.S.P) for nonabsorbable surgical sutures. The sutures may possess a surface texture or other types of tactile or enhanced visual identification means. Further, the sutures may be microengraved or X-ray identifiable with identifying information. The sutures also may employ microchip technology, nanotech technology, RFID technology, specialized coatings, frequency emitting devices that allow current or future-developed 3-dimensional, computer, or virtual reality medical imaging modalities to locate and identify sutures in the body. These marking methods may be provided in combination or in various sub-combinations.

In one example, the clips and/or sutures are configured to selectively deliver medication to the patient. That is, the aspects of various embodiments of the present invention may also allow for the utilization of adjuvant therapies that employ selective and/or controlled application of drugs, radiation, etc. In one embodiment, the clips/sutures left in the patient's body employ treatment means, e.g., drug and/or radiation delivery systems. The clips/sutures of some embodiments employ drug and/or radiation delivery systems or are constructed at least partially from such materials that provide treatment over an extended period of time. For example, all or a portion(s) of the clips/sutures may comprise a drug-infused co-polymer (i.e., a polymer drug conjugate) manufactured of polylactide-polyglycolide similar to that found in dissolvable sutures.

The suture or clip may have diagnostic qualities, wherein a characteristic change occurs when conditions around the specimen mass change. For example, tumor growth, tissue DNA/RNA change, etc., would initiate a color change in the clips/sutures. The clips/sutures may also possess the ability to transmit diagnostic information outside the patient's body.

In another example, the clips and/or sutures are configured to indicate special information, e.g., the distance between clips or sutures, the distance between a clip and the specimen mass within the body, etc., which may assist in ascertaining mass growth. One of ordinary skill in the art will appreciate that the clips may employ other types of indicia alone or in combination with corresponding indicia of the sutures without departing from the scope of the embodiments of the present invention. Further, the characteristics of the clips and/or sutures do not have to match identically across the margin boundary; the primary concern is that one must later be able to orient the mass relative to the area of excision, which will be described below correctly.

The surgeon may implement the clip/suture combination as an effective tool for manipulating tissues, which is more efficient than attaching a handle to an otherwise slippery surface. For example, the sutures and/or clips described herein can facilitate traction, counter traction, specimen mass control during robotic and laparoscopic cases, and lift the specimen mass into extraction bags. The clips/sutures contemplated herein may also be used to facilitate wound closure or as anchor points for implants.

The Summary of the Invention is neither intended nor should it be construed as being representative of the full extent and scope of the present invention. That is, these and other aspects and advantages will be apparent from the disclosure of the invention(s) described herein. Further, the above-described embodiments, aspects, objectives, and configurations are neither complete nor exhaustive. As will be appreciated, other embodiments of the invention are possible using, alone or in combination, one or more of the features set forth above or described below. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description and no limitation as to the scope of the present invention is intended by either the inclusion or non-inclusion of elements, components, etc. in this Summary of the Invention. Additional aspects of the present invention will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present invention are possible utilizing, alone or in combination, as set forth above and/or described in the accompanying figures and/or in the description herein below.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and drawing figures are to be understood as being approximations which may be modified in all instances as required for a particular application of the novel assembly and method described herein.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description and in the appended drawing figures.

BRIEF DESCRIPTION OF THE DRAWINGS

The present invention will be understood more fully from the detailed description given below and from the accom

DETAILED DESCRIPTION

A surgical specimen margin orientation marking mechanism is described. Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

In the following description, numerous details are set forth. It will be apparent, however, to one skilled in the art, that the present invention may be practiced without these specific details. In other instances, well-known structures and devices are shown in block diagram form, rather than in detail, in order to avoid obscuring the present invention.

Figure 1:
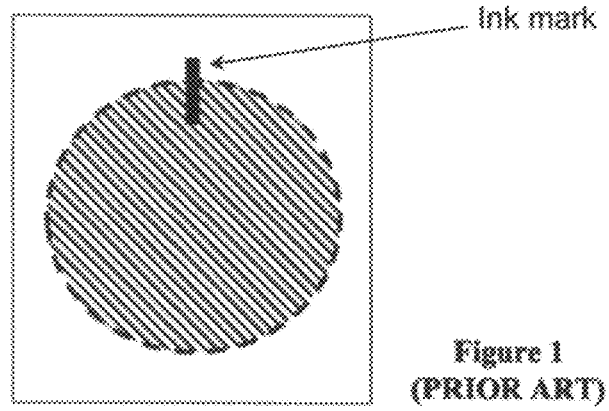
- FIG. 1 illustrates a conventional surgical specimen margin orientation marking system.
Figure 2:
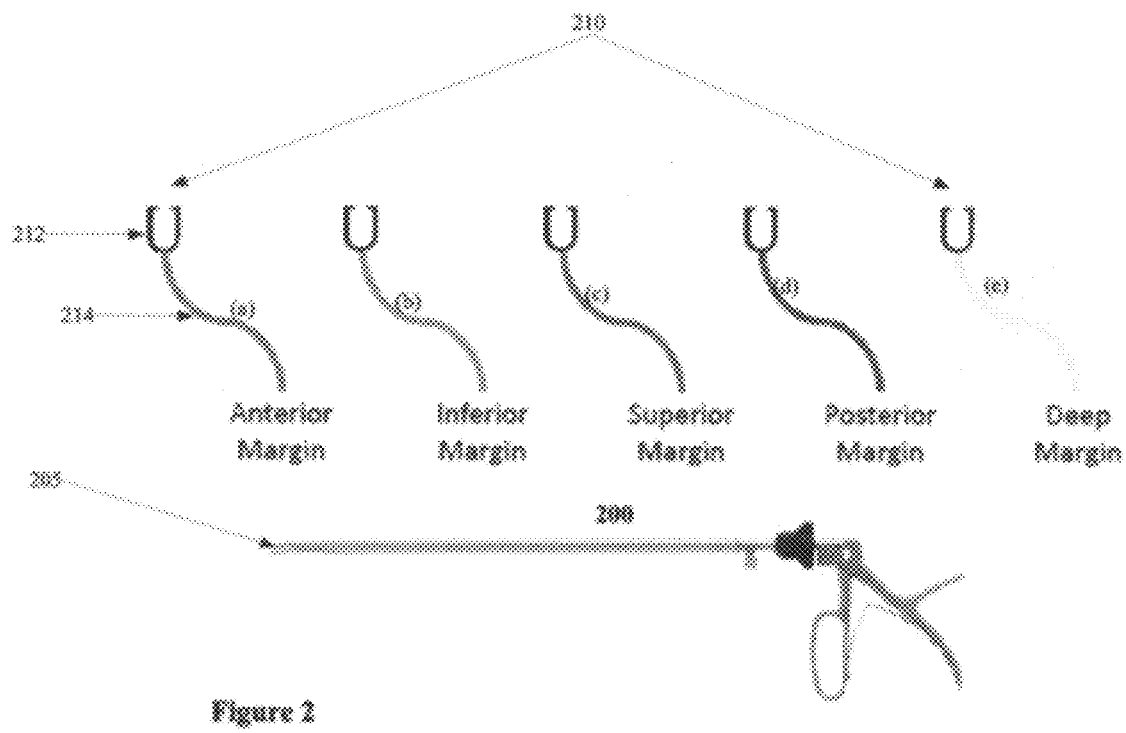
FIG. 2 illustrates one embodiment of a surgical specimen margin orientation marking mechanism.

FIG. 2 illustrates one embodiment of a surgical specimen margin orientation marking mechanism 200. Mechanism 200 includes an endoscopic clip placement tool 205 and marking clips 210. In one embodiment, each marking clip 210 includes a clip 212 and a color-coded suture 214 attached at a closed end of clip 212. In some embodiments, the clips are also color coded and match the color of the suture. In one embodiment, the clips 212 are titanium ligature clips, while the sutures are comprised of silk.

The clips and/or clip teeth may be constructed of material that suits the material to which they are to be attached—muscle, ligament, skin, fatty tissue, etc. The clips can be of any size and shape and made of any suitable material. For example, the clip's material of manufacture may be stiff, compliant, malleable, etc. to suit the surgeon's desires or to accommodate tissue character. The clips may possess a surface texture or other types of tactile or enhanced visual identification means. Further, the clips may be micro-engraved or X-ray marked with identifying information The clips can have a distinct color that identifies a predetermined location on a specimen mass. In one embodiment, the clip color coincides with that of the suture. Still further, the clips may employ microchip technology, nanotech technology, RFID technology, specialized coatings, frequency emitting devices that allows current or future-developed 3-dimentional, computer, or virtual reality medical imaging modalities to locate and identify clips in the body. These marking methods may be provided in combination or in various sub-combinations.

The sutures of some embodiments of the present invention are stiff, compliant, malleable, etc. to suit the surgeon's desires. The sutures may possess a surface texture or other types of tactile or enhanced visual identification means. Further, the sutures may be micro-engraved or X-ray identifiable with identifying information. The sutures also may employ microchip technology, nanotech technology, RFID technology, specialized coatings, frequency emitting devices that allows current or future-developed 3-dimentional, computer, or virtual reality medical imaging modalities to locate and identify sutures in the body. These marking methods may be provided in combination or in various sub-combinations.

In one example, the clips and/or sutures are configured to selectively deliver medication to the patient. That is, the aspects of various embodiments of the present invention may also allow for the utilization of adjuvant therapies that employ selective and/or controlled application of drugs, radiation, etc. In one embodiment, the clips/sutures left in the patient's body, which will be described below, employ treatment means, e.g., drug and/or radiation delivery systems controlled from an outside source. The clips/sutures of some embodiments employ drug and/or radiation delivery systems or are constructed at least partially from such systems that provide treatment over an extended period of time. For example, all or a portion(s) of the clips/sutures may comprise a drug-infused co-polymer (i.e., a polymer drug conjugate) manufactured of polylactide-polyglycolide similar to that found in dissolvable sutures.

The suture or clip may have diagnostic qualities, wherein a characteristic change occurs when conditions around the specimen mass change. For example, tumor growth, tissue DNA/RNA change, etc. would initiate a color change in the clips/sutures. The clips/sutures may also possess the ability to transmit diagnostic information outside the patient's body.

In another example, the clips and/or sutures are configured to indicate special information, e.g., distance between clips or sutures, distance between a clip and the specimen mass within the body, etc, which may assist ascertain growth of a mass. One of ordinary skill in the art will appreciate that the clips 212 may employ other types of indicia alone or in combination with corresponding indicia of the sutures 214 without departing from the scope of the embodiments of the present invention. Further, the characteristics of the clips and/or sutures do not have to match identically across the margin boundary; the primary concern is that one must later be able to correctly orient a mass, which will be described below.

According to one embodiment, the color-coded sutures 214(*a*)-214(*e*) are implemented to indicated a location. In such an embodiment, 214(*a*) includes a red suture indicating an anterior location. Similarly, 214(*b*), 214(*c*), 214(*d*) and 214(*e*) include green, blue, purple and yellow sutures, respectively, that represent inferior, superior, posterior and deep locations, respectively. However, other embodiments may feature various other color-coding schemes. Again, the clips can also be color-coded.

In one embodiment, a surgeon will place two marking clips 210 for specimen mass marking. In such an embodiment, one marking clip 210 is placed on a specimen mass, while the second marking clip 210 is placed in the surrounding tissue. Subsequently, a cut is made in between the two areas. The result is a mirror image marking of the two areas. That is, the paired clips allow for the specimen (ex-vivo) and the cavity created (in-vivo) to correspond to one another in mirror image fashion.

Figure 3A:
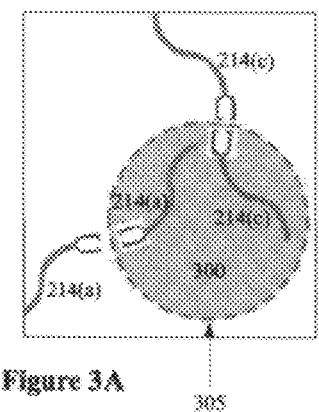
FIGS. 3A-3E illustrate embodiments of a specimen mass identified by marking clips.

Color coded sutures 214 are attached to the clips having colors designating the anterior, inferior, superior, posterior, and deep margins, as discussed above. FIGS. 3A-3E illustrate embodiments of a specimen mass identified by marking clips 210. As shown in FIG. 3A, a specimen mass 300 to be excised is identified by dotted line 305 to differentiate from surrounding tissues.

Figure 3B:
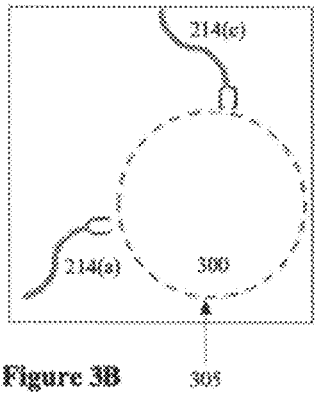
Figure 3C:
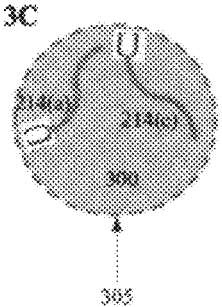

Color-coded sutures 214 devices are placed on the margins to identify orientation. For instance, clips 210 are shown having pairs of sutures 214(*a*) and 214(*c*). Note that only two types of suture 214 clips have been shown for ease of viewing. FIG. 3B shows clips 210 having sutures 214(*a*) and 214(*b*) attached to tissue above specimen mass 300 for orientation following excision of specimen mass 300, while FIG. 3C shows clips 210 having sutures 214(*a*) and 214(*b*) attached to specimen mass 300 for orientation following excision. The clips/sutures attached to tissue associated with the specimen mass can be left in the patient's body for future identification.

Figure 3D:
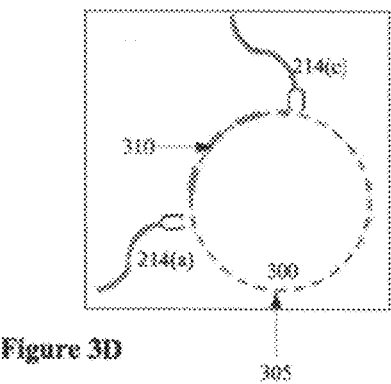
Figure 3E:
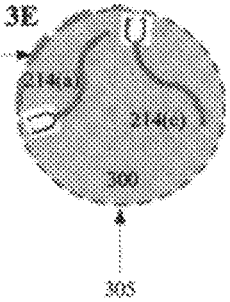

According to one embodiment, marking mechanism 200 enables accurate communication between a pathologist and a surgeon, assuming a positive or close margin determined by the pathologist. FIG. 3D shows additional tissue 310 requiring excision that can be more accurately addressed, and FIG. 3E shows a positive or close margin identified by the pathologist.

In a further embodiment, the surgeon may implement the clip 210/suture 214 combination as an effective tool for manipulating tissues, which is more efficient than attaching a handle to an otherwise slippery surface. For example, the sutures and/or clips described herein can be used to facilitate traction, counter traction, specimen mass control during robotic and laparoscopic cases, and lifting the specimen mass into extraction bags.

The clips/sutures contemplated herein may also be used to facilitate wound closure or as anchor points for implants.

Figure 4:
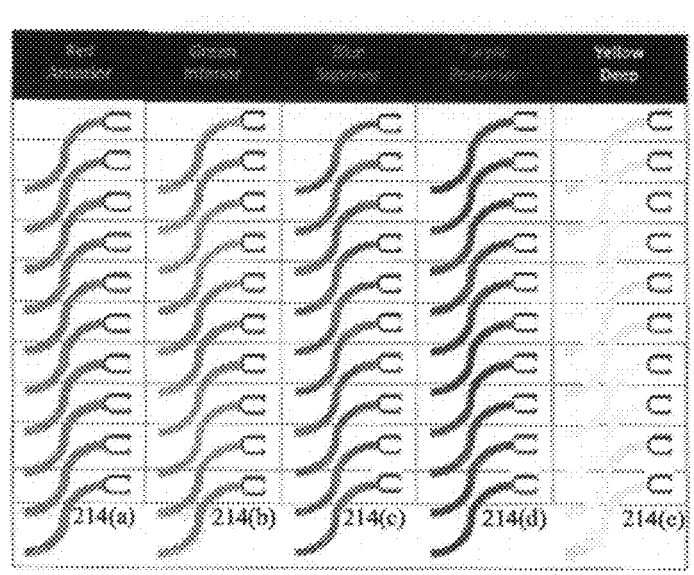
FIG. 4 illustrates one embodiment of a package of marking clips.
Figure 5:
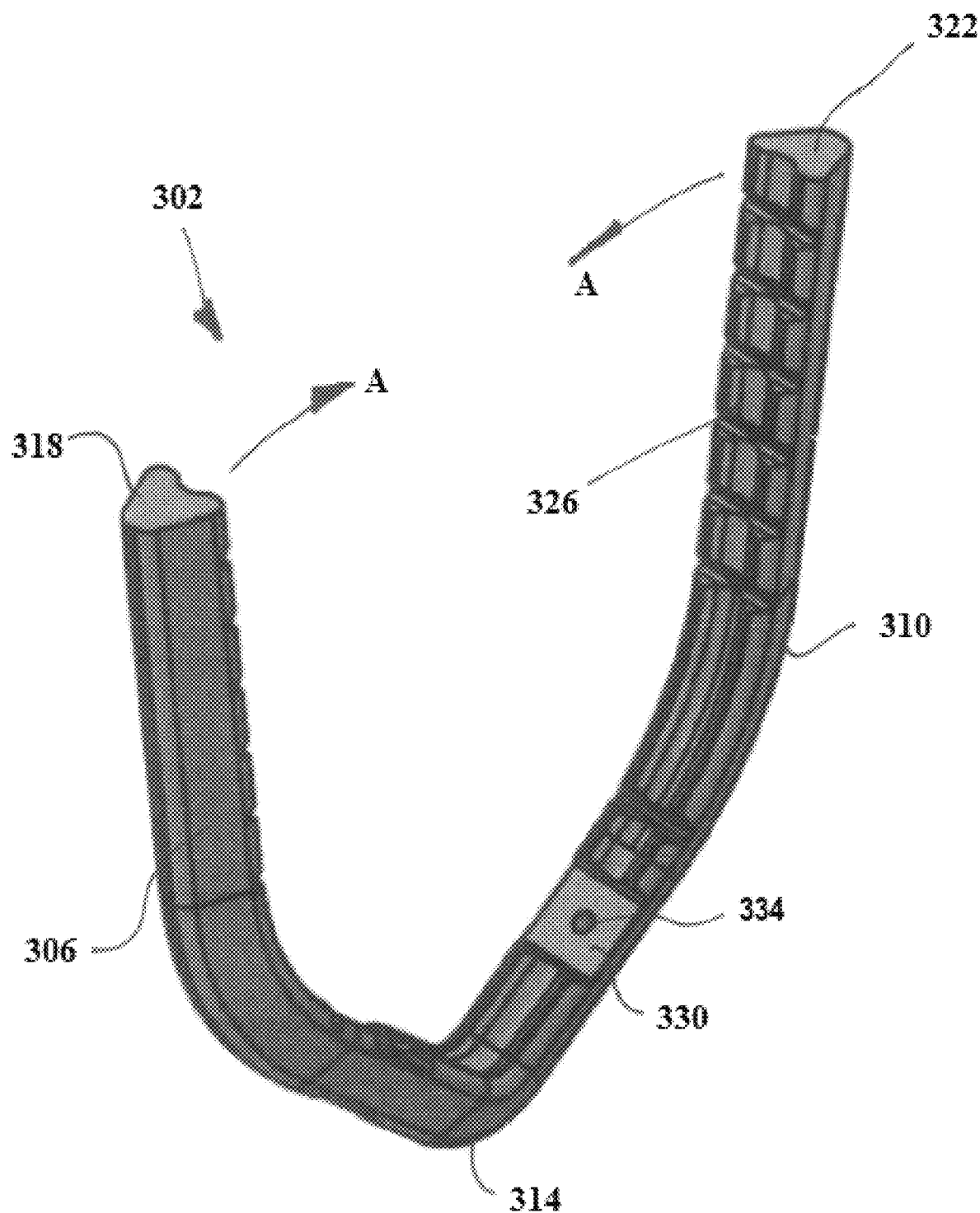
FIG. 5 is a perspective view of the clip of one embodiment of the present invention.

FIG. 4 illustrates one embodiment of a package of marking clips. As shown in FIG. 4, a package may include 25-pair/50-unit cassette of clips 210 having the various sutures 214 for endoscopic procedures.

FIGS. 5-11 show clip 302 of one embodiment of the present invention comprised of a first leg 306 and the second leg 10. The first leg 306 and the second leg 310 have operatively interconnected proximal ends 314 and corresponding distal ends 318 and 322. In one embodiment, the proximal ends are interconnected by a living hinge, a hinge, or a deformable member. The deformable members may be of a thickness less than that of the legs to allow the distal ends to be urged towards each other. In some embodiments, the deformable portions are spaced from the leg's proximal ends. Further, those of ordinary skill in the art will appreciate that the legs are inherently deformable. In operation, pressure applied to the outside surface of the first and/or second leg will selectively deform the clip 302 and move the distal end of the first leg 318 and the distal end of the second leg 322 towards each other, generally in the direction of Arrow A. One of ordinary skill in the art will appreciate that the dimensions shown in FIGS. 6-8 and 10 are applicable to one embodiment of the present invention and, thus, are for reference only.

Figure 6:
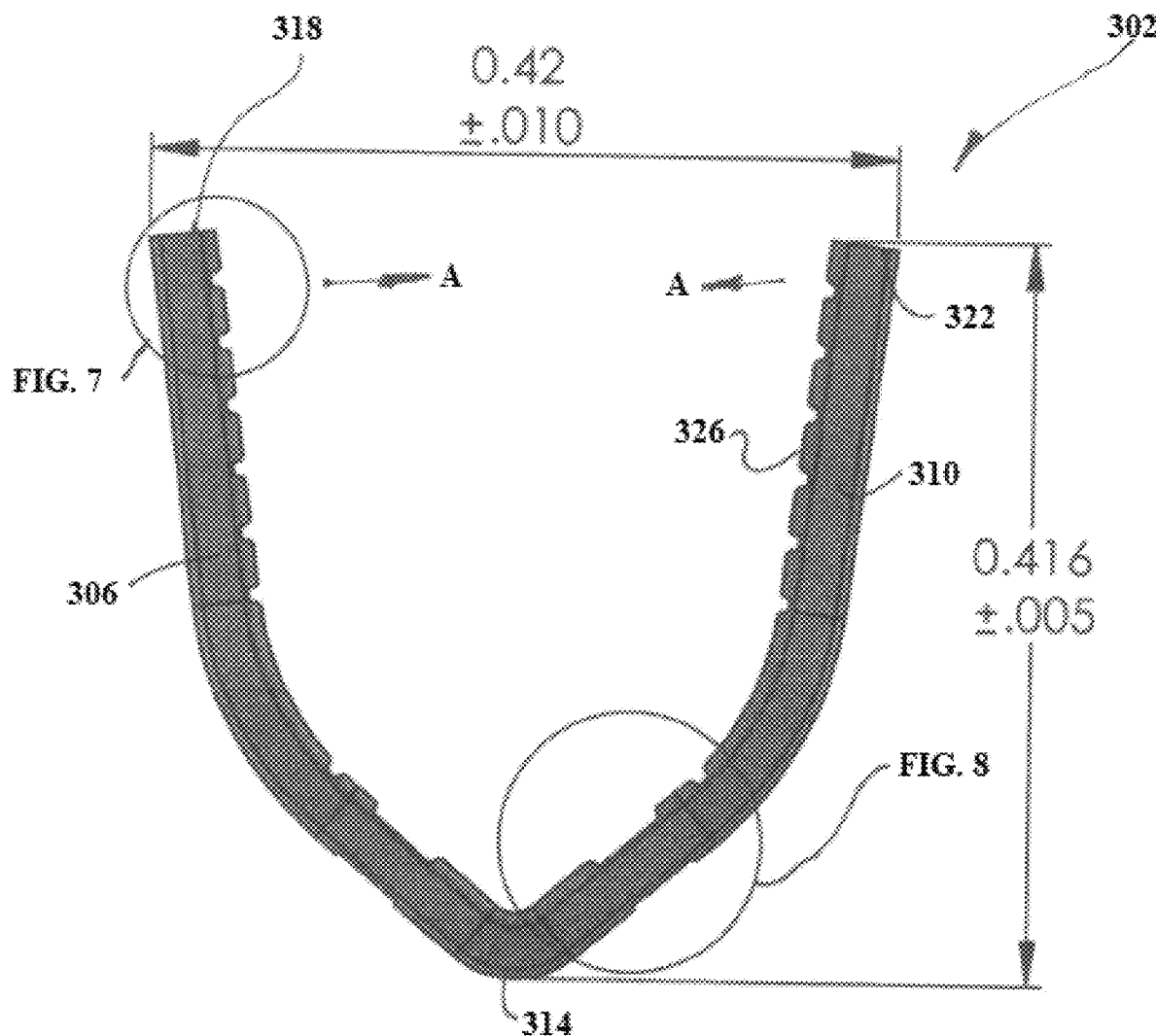
FIG. 6 is a front elevation view of the clip shown in FIG. 5.
Figure 7:
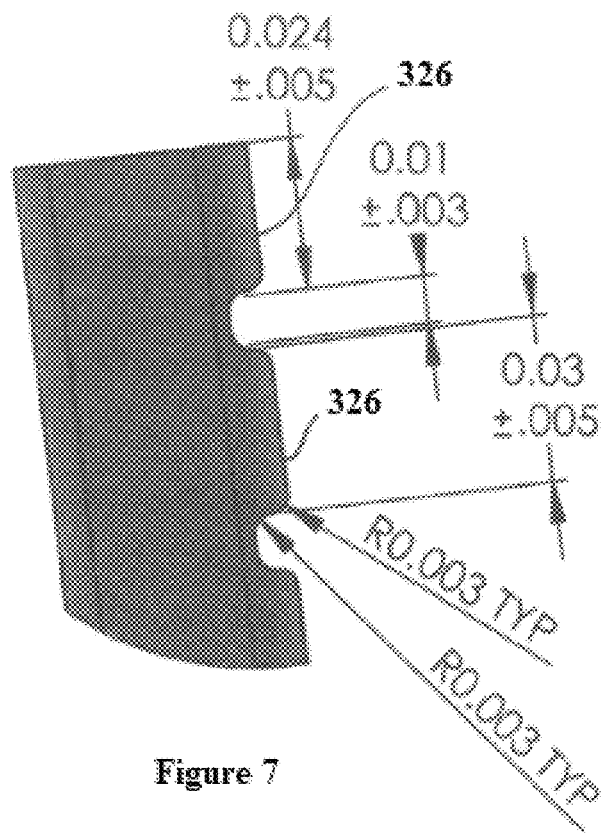
FIG. 7 is a detailed view of FIG. 6.

FIGS. 6 and 7 highlight the nature of the inner surfaces of the first and second legs of one embodiment, wherein teeth 326 are provided to facilitate clip grasping onto a tissue sample taken from a patient's body and/or in vivos tissue associated with the excised sample, which will be apparent upon review of FIGS. 15-22. In operation, biasing of the legs towards each other will bring corresponding teeth 326 into close proximity with tissue therebetween.

Figure 8:
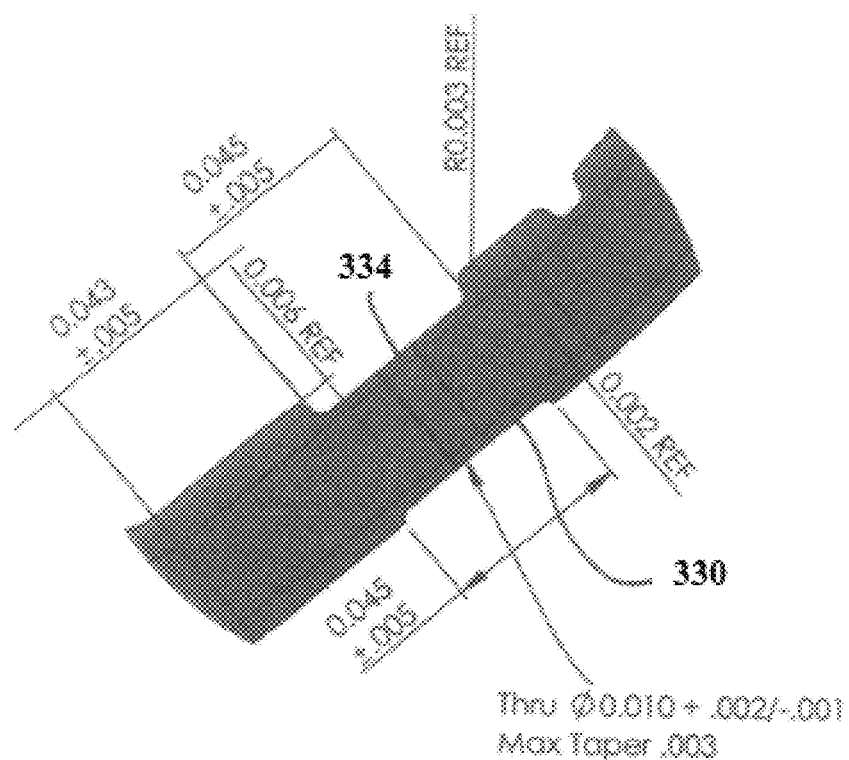
FIG. 8 is a detailed view of FIG. 6
Figure 9:
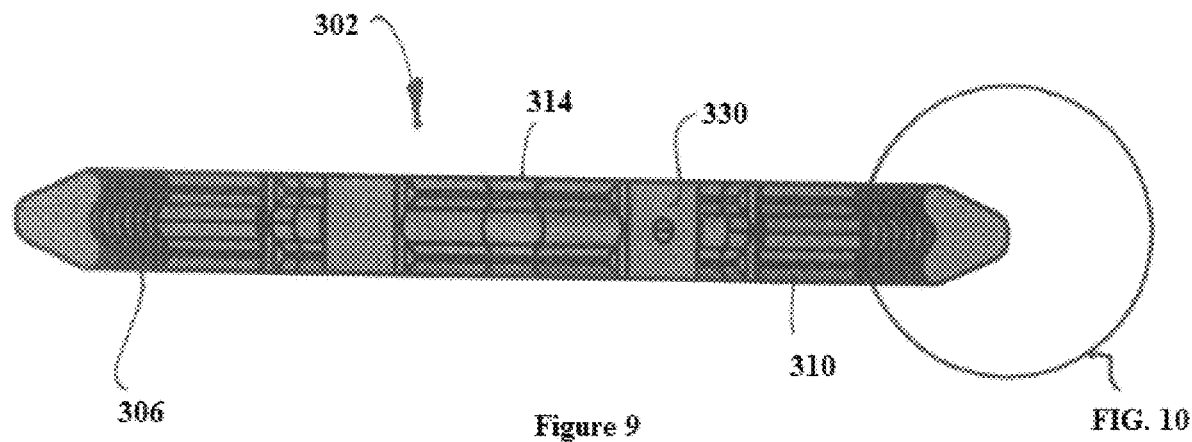
FIG. 9 the top plan view of the clip shown in FIG. 5.
Figure 10:
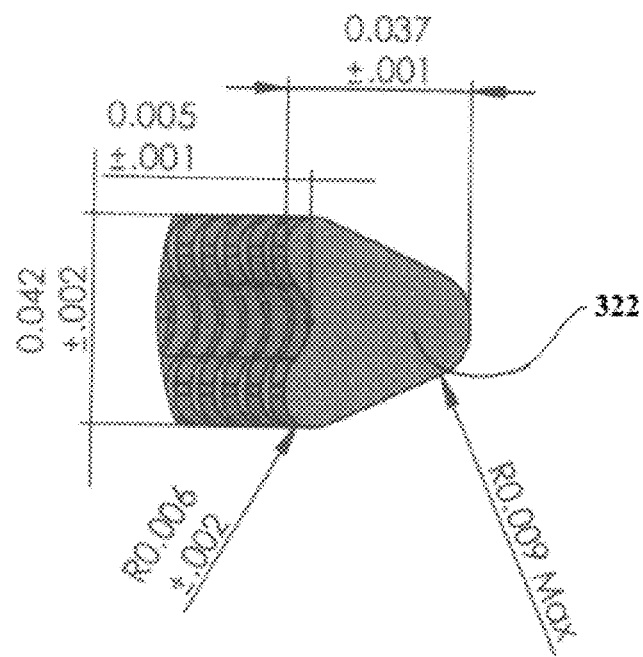
FIG. 10 is a detailed view of FIG. 9.
Figure 11:
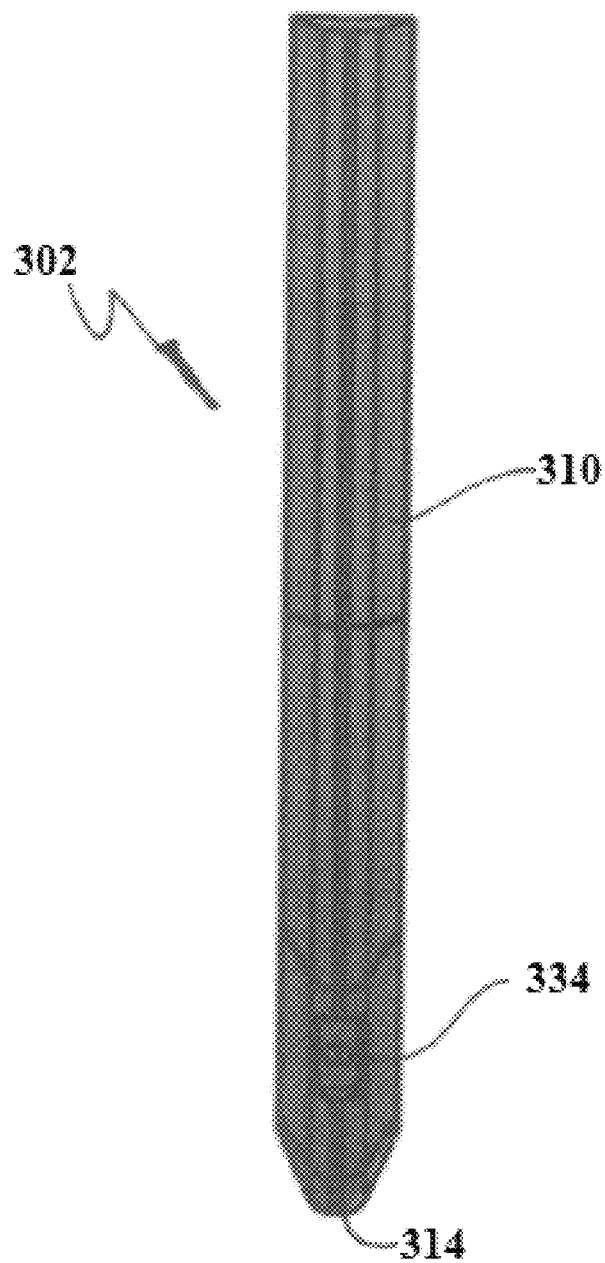
FIG. 11 is a right elevation view of the clip shown in FIG. 5.
Figure 12:
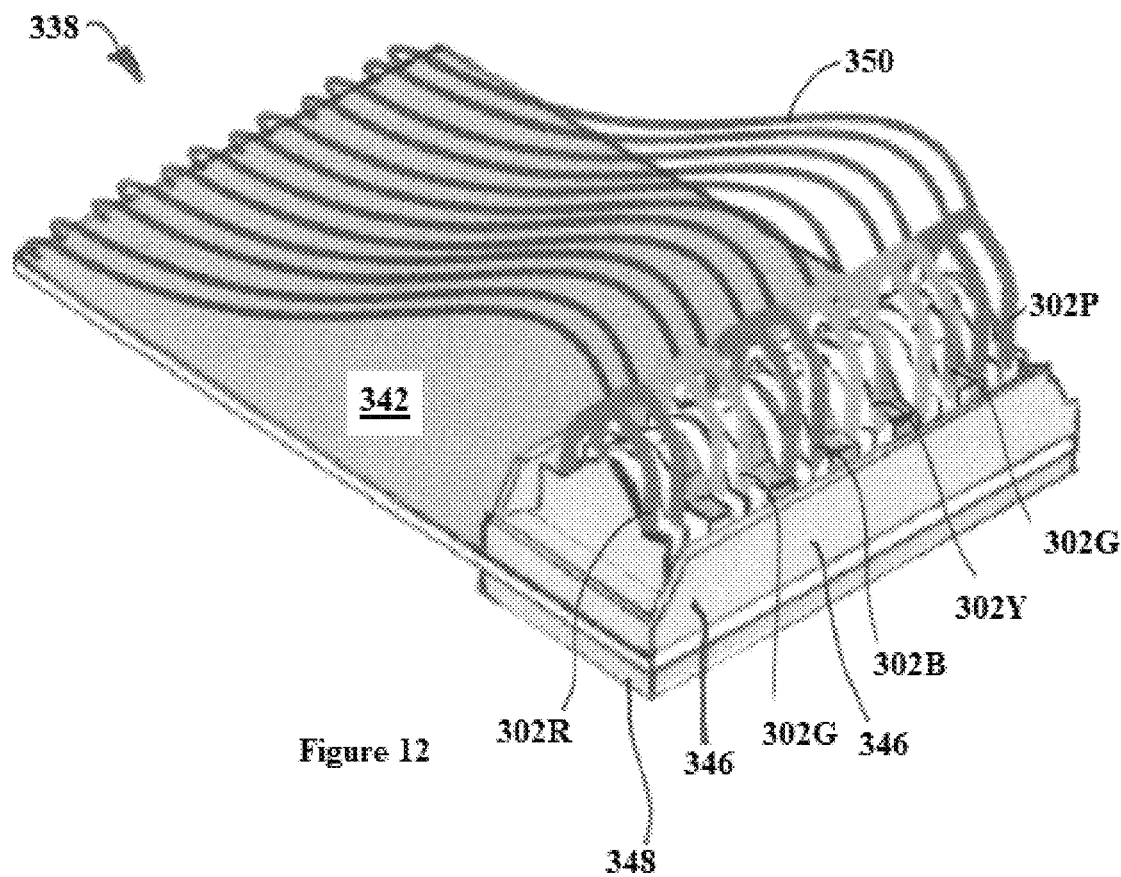
FIG. 12 is a perspective view of the clip system of one embodiment of the present invention.

FIG. 8 shows another portion of the clip adjacent to the proximal end 314. Here, a tapered portion 330 is provided that accommodates a suture hole 334. The suture hole 334 receives a suture as shown in FIG. 12 that helps identify the clip. The tapered section 330 may also facilitate movement of the distal ends towards each other.

FIG. 12 shows a clip system 338 of one embodiment of the present invention having a base 342 with interconnected housing 346 that accommodates a plurality of clips 302 and associated sutures 350. For example, adhesive 348 can be used to secure the base 342 to a tray. In this example, colored suture pairs consisting of margin side and in vivo side are shown, wherein the colors denote predefined approximate locations of clip placement, which will be described in further detail below. As mentioned above, suture color may denote margin side or in vivo side or match the clip color. One of ordinary skill in the art will appreciate that although solid colors are alluded to herein, other identification methods, such as stripes or striations, may be employed without departing from the scope of the invention.

Figure 13:
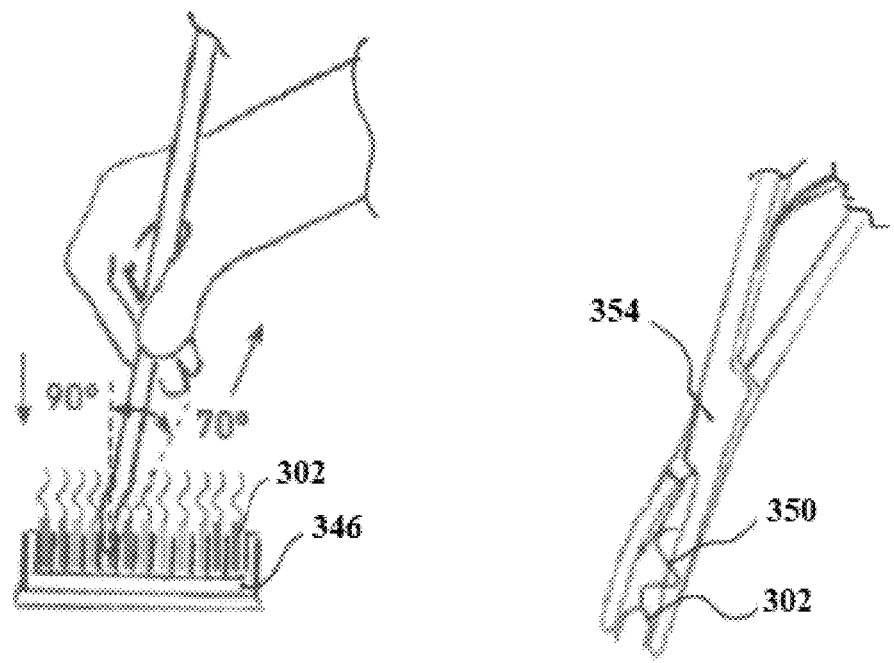
FIG. 13 is a front elevation view of the clip system illustrating the removal of one clip from a housing.

FIG. 13 illustrates the removal of a clip 302 from the housing. Here, the housing includes cavities that selectively receive and securely maintain the clips within the housing. This feature ensures clip sterility and decreases the chances of the incorrect clip being removed because the physician must make a concerted effort to remove a desired clip from the housing. An applier 354 is used to grasp and angulate the clip 302 a predetermined amount, in the example shown about 20° from horizontal, to initiate clip removal. Thereafter, the clip 302 remains held by the applier 354 in an orientation suitable for interconnection to tissue.

Figure 14:
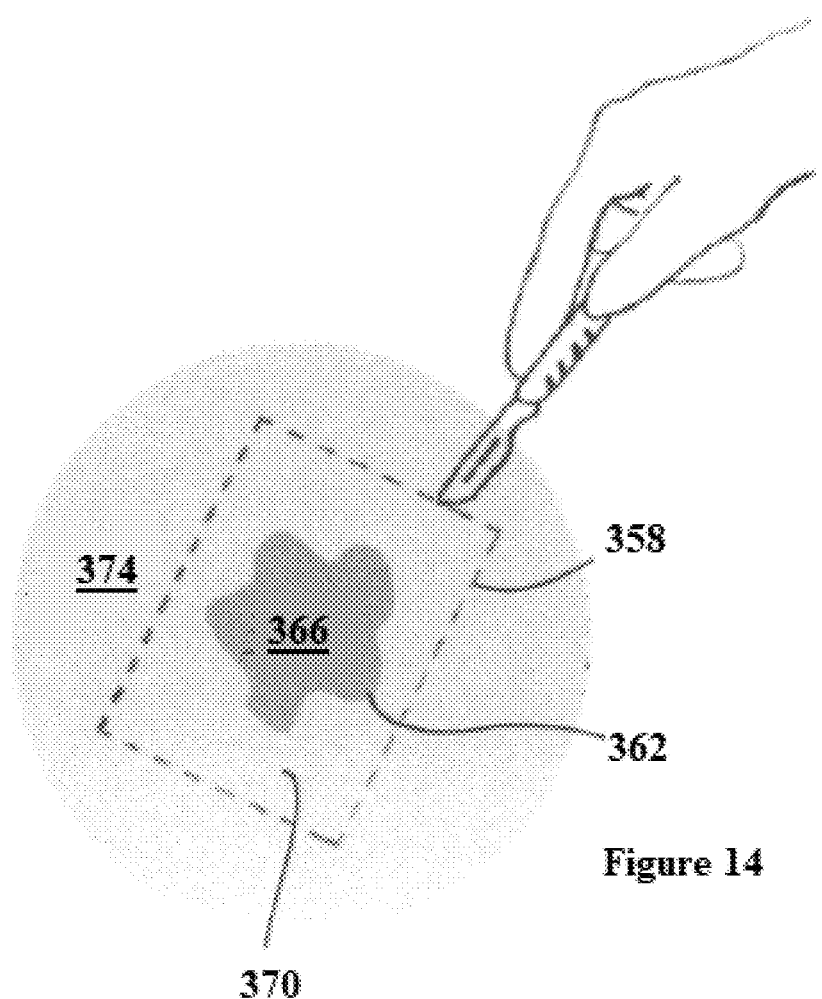
FIG. 14 is a representation showing the first step in removing a tissue sample from the body.
Figure 15:
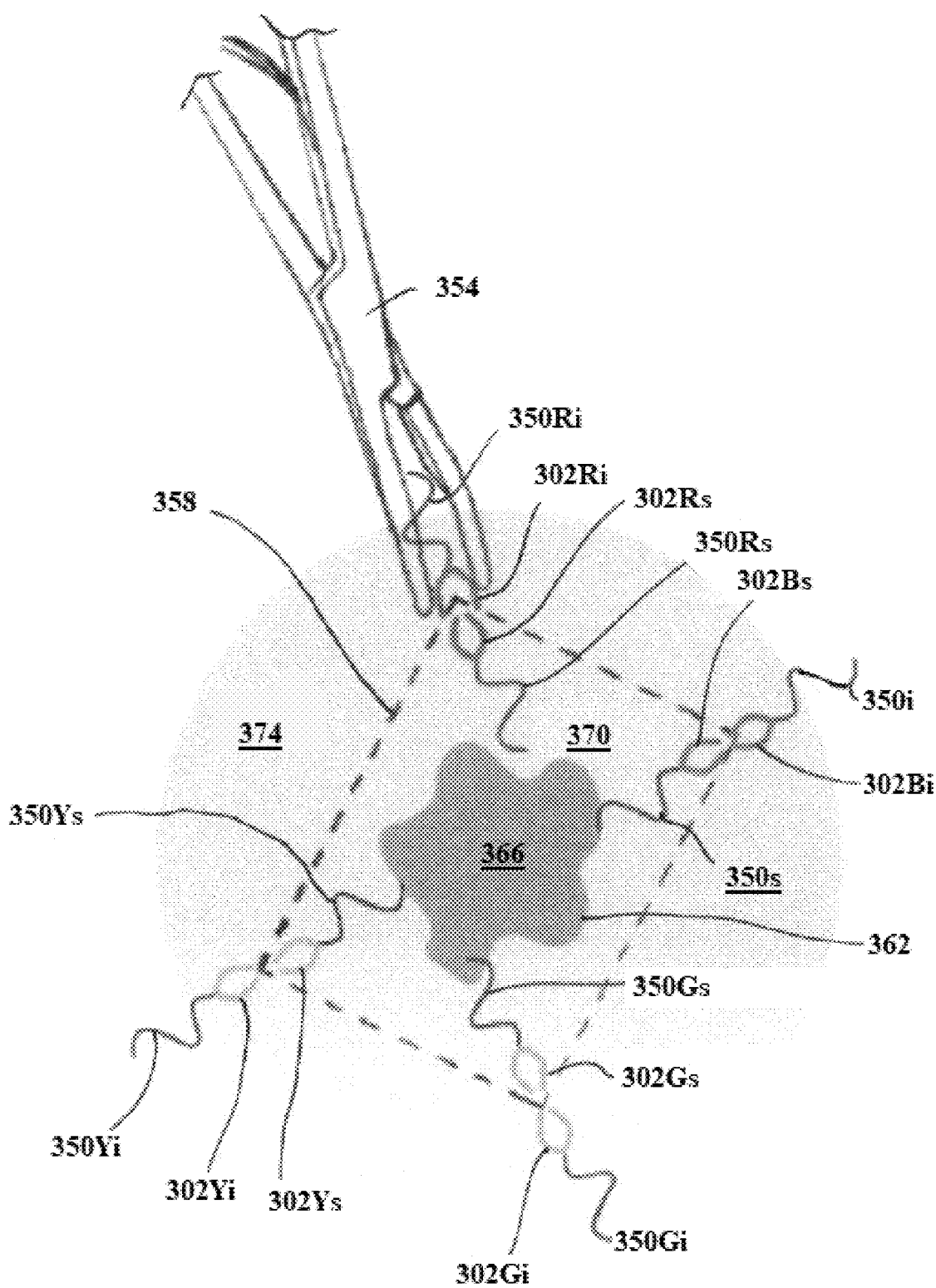
FIG. 15 is a representation showing the incorporation of clips to an in vivo side and a margin side of the tissue sample.

FIGS. 14 and 15 illustrate pre-sample removal from the patient. The first step in the operation is to define a margin 358 a predetermined distance from a periphery 362 of a mass 366, i.e., the area of concern being biopsied. The margin 358, thus, defines a sample 370 that will be removed from the patient. Before removal, however, a plurality of clips are associated with the sample 370 and in vivo tissue 374 associated with the sample. According to one embodiment, color-coded clips 302Rs, 302Bs, 302Gs, and 302Ys indicate locations on the sample (s), and corresponding color-coded clips 302Ri, 302Bi, 302Gi, and 302Yi indicate mirrored, in vivo (i) locations. One of skill in the art will appreciate the sample side clips 302s and the in vivo side clips 302i may have the same color or otherwise be identified as a pair with predefined indicia (e.g., A and 1, B and 2, etc.), integrated RFID technology, x-ray markers, etc.

Color-coated sutures can be provided on the sample side 350Rs, 350Bs, 350Gs, and 350Ys and the in vivo side 350Ri, 350Bi, 350Gi, and 350Yi. Suture color or marking method may correspond with the interconnected clip color or marking method. Alternatively, suture color may depend on whether the clip is on the sample side 350s or the in vivo side 350i. In FIG. 15, the sutures are of the same color. In one embodiment, red clamps/sutures indicate an anterior sample location. Similarly, green, blue, purple, and yellow clamps/sutures represent inferior, superior, posterior, and deep locations, respectively. However, other embodiments may feature various other color-coding schemes.

Figure 16:
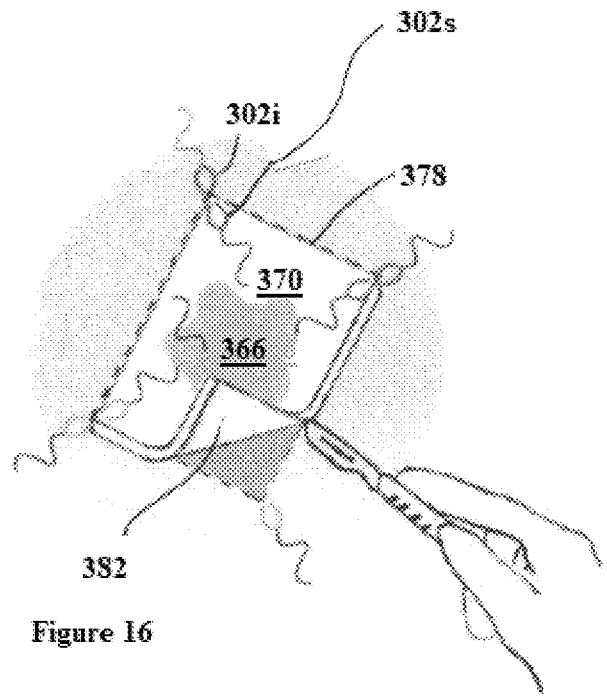
FIG. 16 is a representation showing removal of the tissue sample from a patient.
Figure 17:
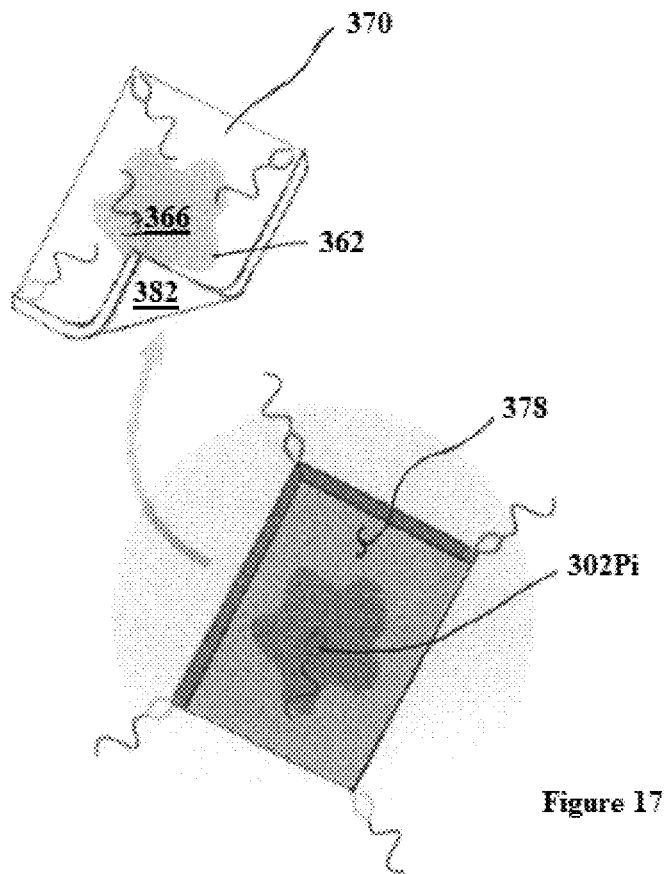
FIG. 17 is a representation showing the removed sample and the incorporation of a deep margin clip in vivo.
Figure 18:
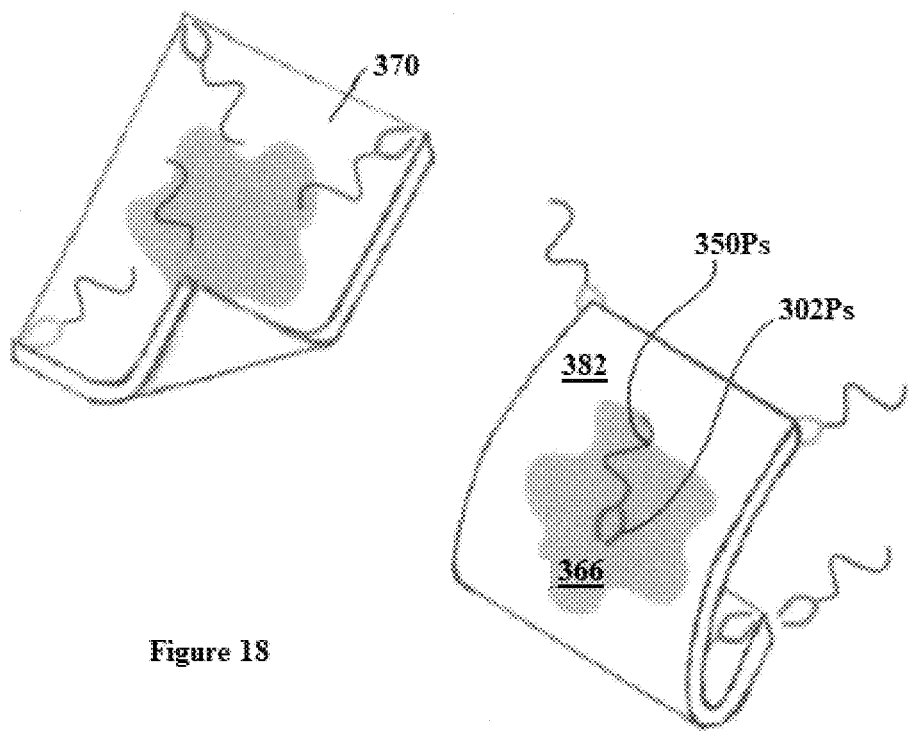
FIG. 18 illustrates both sides of the removed sample.
Figure 19:
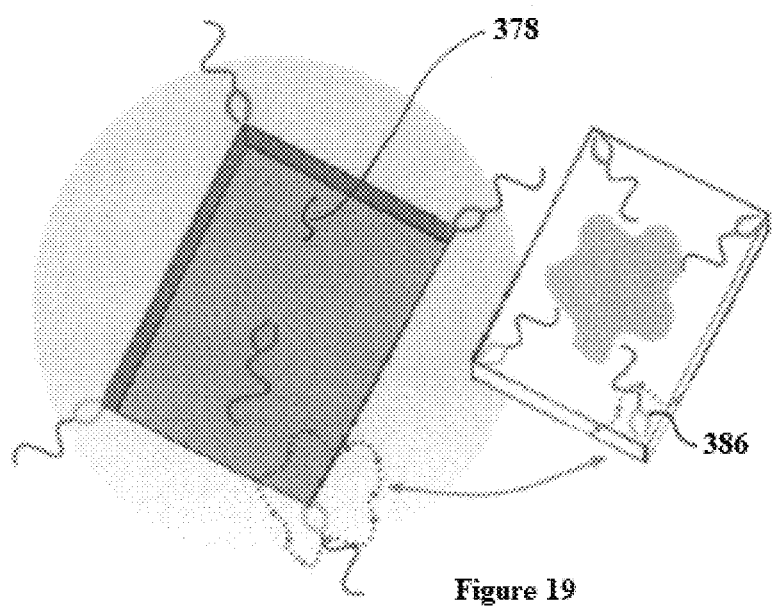
FIG. 19 is a representation of mapping sample's area concerned to a corresponding in vivo location.
Figure 20:
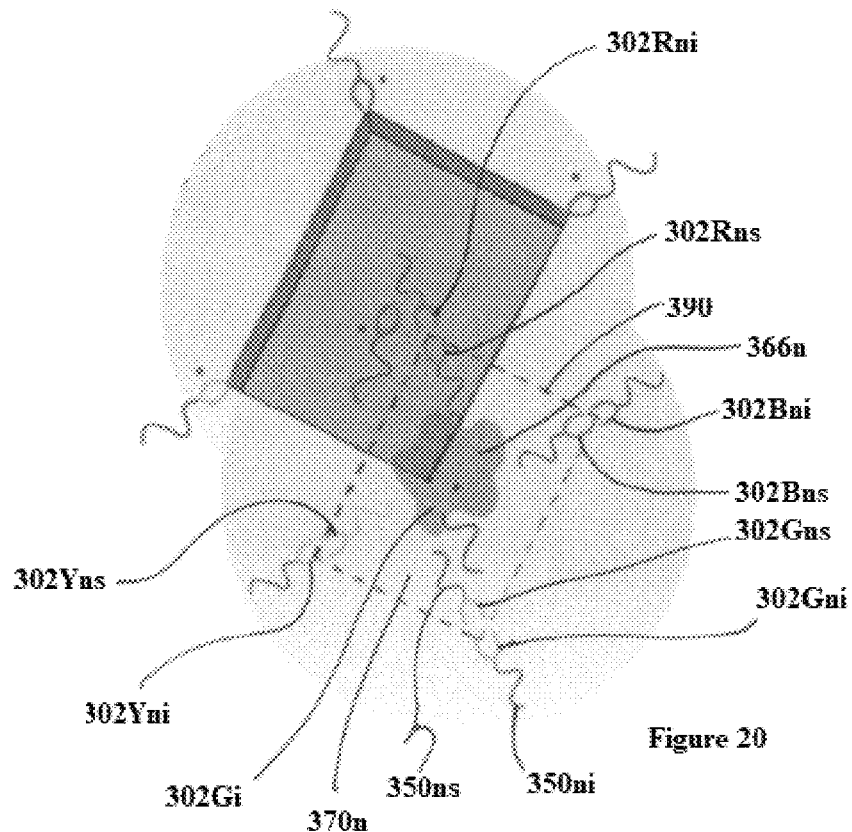
FIG. 20 is a representation showing a defined second margin that surrounds a new area of concern.
Figure 21:
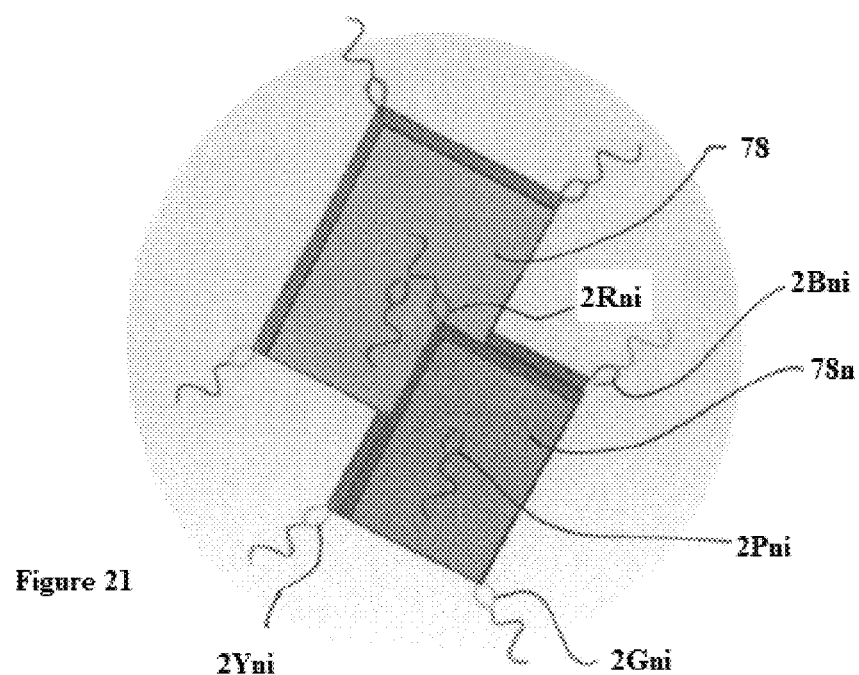
FIG. 21 is a representation showing a removed second sample and the incorporation of a second deep margin clip.

In operation, a surgeon will attach one marking clip 302s to the margin 358 associated with a predefined portion of the specimen mass 366, and a second marking clip 302i to tissue 374 surrounding the specimen mass 366, outside the margin 358. Subsequently, an incision is made along the margin 358, which is shown in FIGS. 14 and 16. The result is a mirror image marking of the two areas—sample and in vivo tissue. The paired clips allow pathologists to quickly match the orientation of the specimen (ex-vivo) relative to a cavity 378 created (in-vivo). FIGS. 17 and 18 show a deep-tissue clip 302Pi placed within the cavity 378, wherein the corresponding sample clip 302Ps is placed on the underside 382 of the sample.

FIGS. 19-22 illustrate one aspect of some embodiments of the present invention that helps a pathologist identify a new area of concern 386. The new area of concern 386 defines a new margin 390, in the example shown, associated with the green clip 302Gs. Accordingly, the surgeon can create an accurate new margin 390 because the corresponding in vivo green clip 302Gi can be quickly located. A series of new clips 302Rni, 302Rns, 302Bni, 302Bns, 302Gni, 302Gns, 302Yni, 302Yns, 302Pni, and 302Pns (not shown) can then be associated with a new tissue sample (not shown) and the new cavity 378n. As one of ordinary skill in the art will appreciate, the process of defining new margins will continue until the pathologist is satisfied that all areas of concern have been excised.

Figure 22:
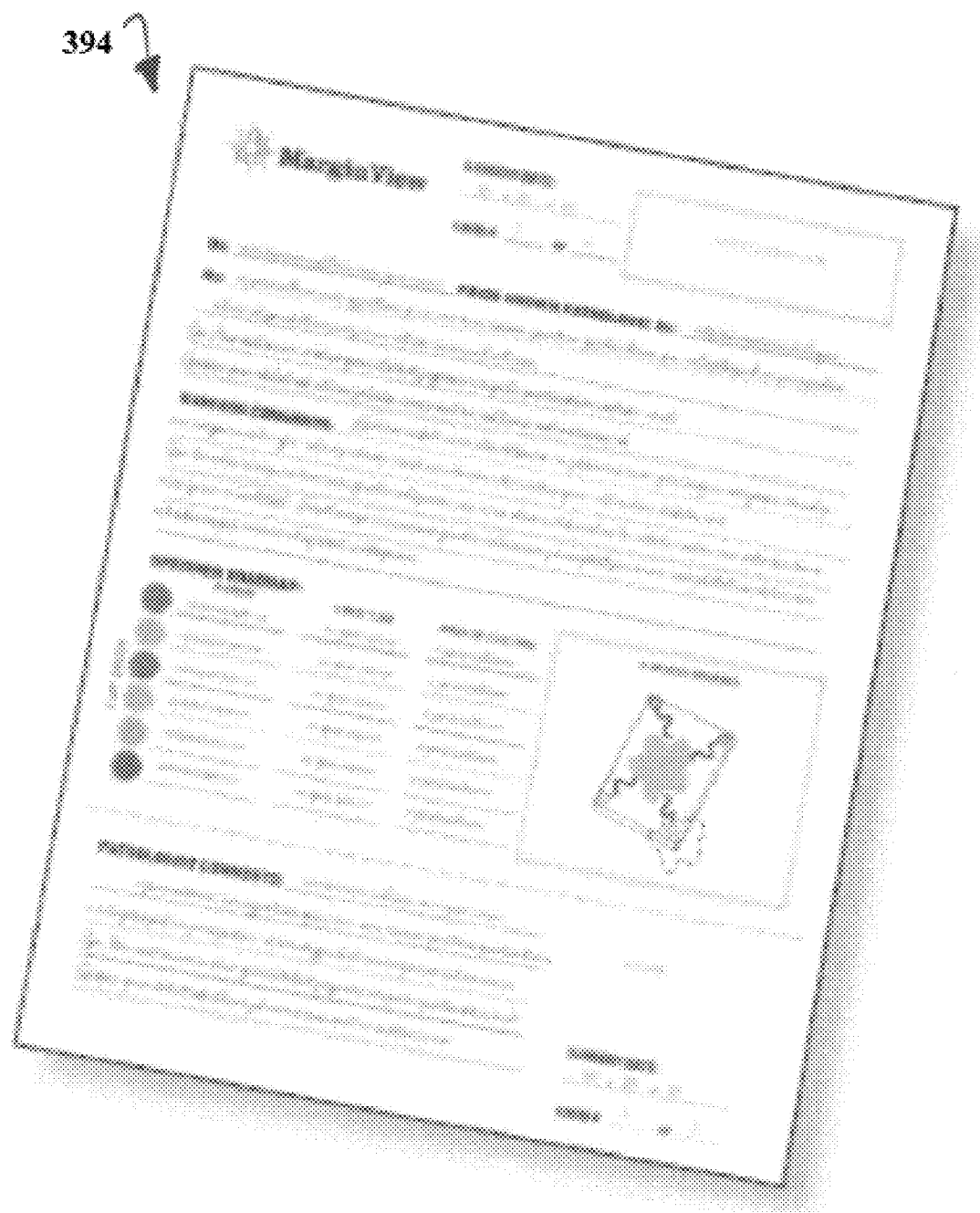
FIG. 22 shows an example of a report concerning the clips of one embodiment of the present invention.

FIG. 22 is a representation of a report 394 associated with the biopsy or mass removal procedure. The report 394 is designed to provide a historical record of the entire surgical procedure. If the area of concern becomes an issue in the future, the nature of the in vivo clips can be assessed and compared with the prior procedure. For example, if the area of concern shifts to a new clip set, the pathology of the mass may be assessed and amended to provide a new strategy for addressing the medical issue. The report 394 will provide a detailed description of color and clip location for immediate or future use.

Exemplary characteristics of embodiments of the present invention have been described. However, to avoid unnecessarily obscuring embodiments of the present invention, the preceding description may omit several known apparatus, methods, systems, structures, and/or devices one of ordinary skill in the art would understand are commonly included with the embodiments of the present invention. Such omissions are not to be construed as a limitation of the scope of the claimed invention. Specific details are set forth to provide an understanding of some embodiments of the present invention. It should, however, be appreciated that embodiments of the present invention may be practiced in a variety of ways beyond the specific detail set forth herein.

Modifications and alterations of the various embodiments of the present invention described herein will occur to those skilled in the art. It is to be expressly understood that such modifications and alterations are within the scope and spirit of the present invention, as set forth in the following claims. Further, it is to be understood that the invention(s) described herein is not limited in its application to the details of construction and the arrangement of components set forth in the preceding description or illustrated in the drawings. That is, the embodiments of the invention described herein are capable of being practiced or of being carried out in various ways. The scope of the various embodiments described herein is indicated by the following claims rather than by the foregoing description. And all changes which come within the meaning and range of equivalency of the claims are to be embraced within their scope. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The foregoing disclosure is not intended to limit the invention to the form or forms disclosed herein. In the foregoing Detailed Description, for example, various features of the invention are grouped together in one or more embodiments for the purpose of streamlining the disclosure. This method of disclosure is not to be interpreted as reflecting an intention that the claimed inventions require more features than expressly recited. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention. Further, the embodiments of the present invention described herein include components, methods, processes, systems, and/or apparatus substantially as depicted and described herein, including various sub-combinations and subsets thereof. Accordingly, one of skill in the art will appreciate that would be possible to provide for some features of the embodiments of the present invention without providing others. Stated differently, any one or more of the aspects, features, elements, means, or embodiments as disclosed herein may be combined with any one or more other aspects, features, elements, means, or embodiments as disclosed herein.

What is claimed is:

1. A method of marking and orienting a specimen mass with an outer margin, comprising:
   providing a first marking device adapted to attach to a first area associated with the specimen mass;
   attaching the first marking device to the first area;
   providing a second marking device adapted to attach to a second area associated with tissue surrounding the specimen mass and outside the outer margin;
   attaching the second marking device to the second area;
   wherein the first area and the second area are located on direct opposite sides of the outer margin, such that the first marking device and the second marking device identify the orientation of the specimen mass relative to the tissue surrounding the specimen mass; and
   wherein the first and second marking devices include a first leg having a proximal end with a plurality of inwardly-extending teeth and a distal end;
   a second leg having a proximal end with a plurality of inwardly-extending teeth and a distal end;

wherein the first leg and the second leg are curved, and wherein the distal end of the first leg and the distal end of the second leg define an apex, wherein the first and second legs extend away from the apex in the same direction; and a tapered portion on the first leg or the second leg, wherein the tapered portion is configured to facilitate selective leg deformation.

2. The method of claim 1, wherein the first marking device and the second marking device are not interconnected, and the second marking device remains interconnected to the second area.

3. The method of claim 1, wherein a color of the first marking device and a color of the second marking device are identical.

4. The method of claim 1, wherein the first marking device is associated with an anterior area of the outer margin, an inferior area of the outer margin, a superior area of the outer margin, a posterior area of the outer margin, or a deep area of the outer margin; and wherein the second marking device is associated with an anterior area of the outer margin, an inferior area of the outer margin, a superior area of the outer margin, a posterior area of the outer margin, or a deep area of the outer margin, but which is different from the area of the outer margin associated with the first marking device.

5. The method of claim 1, further comprising:

providing a third marking device adapted to attach to a third area associated with the specimen mass;

attaching the third marking device to the third area;

providing a fourth marking device adapted to attach to a fourth area associated with the surrounding tissue;

attaching the fourth marking device to the fourth area;

wherein the color of the first marking device and second marking device is a first color;

wherein a color of the third marking device and a color of the fourth marking device is a second color that is different from the first color; and wherein the first marking device and the second marking device identify a first position of the specimen mass relative to the tissue surrounding the specimen mass and the third marking device and the fourth marking device identify a second position of the specimen mass relative to the tissue surrounding the specimen mass.

6. The method of claim 5, wherein the first marking device, the second marking device, third marking device, and fourth marking device each comprise an end with an associated indicator.

7. The method of claim 1, further comprising a suture interconnected to at least one of the first leg or the second leg.

8. The method of claim 7, wherein at least one of the suture, the first marking device, and the second marking device includes identifying indicia.

9. The method of claim 8, wherein the identifying indicia comprises at least one of a surface texture, a micro-engraving, x-ray markings, microchip technology, nanotech technology, RFID chips, and a coating.

10. The method of claim 1, wherein the distal ends of the first leg and the second leg are spaced such that a distance between the distal ends is less than a length of the first leg or the second leg.

11. A method of marking a specimen mass bounded by an outer margin, comprising:

providing a first marking device adapted to attach to a first location of the specimen mass;

attaching the first marking device to the first location;

providing a second marking device distinct from the first marking device adapted to attach to a second location associated with tissue surrounding the specimen mass;

attaching the second marking device to the second location;

wherein the first location and the second location are positioned on direct opposite sides of the outer margin;

wherein the first and second marking devices include a first leg having a proximal end with a plurality of inwardly-extending teeth and a distal end;

a second leg having a proximal end with a plurality of inwardly-extending teeth and a distal end;

wherein the first leg and the second leg are curved, and wherein the distal end of the first leg and the distal end of the second leg define an apex, wherein the first and second legs extend away from the apex in the same direction; and a tapered portion on the first leg or the second leg, wherein the tapered portion is configured to facilitate selective leg deformation.

12. The method of claim 11, wherein the first marking device and the second marking device identify the orientation of the specimen mass relative to the tissue surrounding the specimen mass.

13. The method of claim 11, wherein the first marking device and the second marking device comprise clips.

14. The method of claim 11, wherein the first marking device is configured to manipulate the mass specimen.

15. The method of claim 11, wherein the first marking device and the second marking device are not interconnected.

16. The method of claim 11, wherein the first marking device and/or the second marking device includes an identifier.

17. The method of claim 16, wherein the identifier is an integrated microchip or comprises nanotechnology.

* * * * *